US010487361B2

(12) United States Patent
Neitz et al.

(10) Patent No.: US 10,487,361 B2
(45) **Date of Patent: *Nov. 26, 2019**

(54) METHODS FOR DIAGNOSING AND TREATING EYE-LENGTH RELATED DISORDERS

(71) Applicant: The University of Washington through its Center for Commercialization, Seattle, WA (US)

(72) Inventors: Jay Neitz, Seattle, WA (US); Maureen Neitz, Seattle, WA (US)

(73) Assignee: University of Washinton Through its Center for Commercialization, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/631,542

(22) Filed: Jun. 23, 2017

(65) Prior Publication Data

US 2017/0292160 A1 Oct. 12, 2017

Related U.S. Application Data

(63) Continuation of application No. 14/581,116, filed on Dec. 23, 2014, now abandoned, which is a continuation of application No. 13/349,877, filed on Jan. 13, 2012, now Pat. No. 8,951,729.

(60) Provisional application No. 61/432,984, filed on Jan. 14, 2011.

(51) Int. Cl.

*C12Q 1/68* (2018.01)
*C12Q 1/6883* (2018.01)
*A61B 5/0496* (2006.01)
*G02C 7/02* (2006.01)
*G02C 7/10* (2006.01)

(52) U.S. Cl.

CPC .......... *C12Q 1/6883* (2013.01); *A61B 5/0496* (2013.01); *C12Q 2600/118* (2013.01); *C12Q 2600/156* (2013.01); *C12Q 2600/172* (2013.01); *G02C 7/02* (2013.01); *G02C 7/10* (2013.01); *G02C 2202/24* (2013.01)

(58) Field of Classification Search

None

See application file for complete search history.

(56) References Cited

U.S. PATENT DOCUMENTS 5,800,992 A 9/1998 Fodor et al.
6,582,908 B2 6/2003 Fodor et al.
6,706,867 B1 3/2004 Lorenz
8,951,729 B2 * 2/2015 Neitz .................. C12Q 1/6883 435/6.11
2003/0082576 A1 5/2003 Jones et al.
2004/0110179 A1 6/2004 Shuber
2005/0208555 A1 9/2005 Raimond, III
2010/0021889 A1 1/2010 Juo

FOREIGN PATENT DOCUMENTS

WO 2010/075319 7/2010

OTHER PUBLICATIONS

Neitz and Neitz, J. Vis. 2:531-42, 2002.
Kuchenbecker et al, Vis. Neurosci. 25(3):301-6, 2008.
Gunther and Dobkins Vision Research 42:1367-1378, 2002.
Neitz et al., Vision Research 35: 2395-2407, 1995.
Schwartz, M. Haim, D. Skarsholm, Clinical Genetics 38, 281, 1990.
Young et al., Archives of Ophthalmology 122, 897, 2004.
Radhakrishna et al., Investigative Ophthalmology & Visual Science supplement, 2005.
Michaelides et al., Ophthalmology 112, 1448, 2005.
Mummidi et aL, Journal of Biological Chemistry (2000) vol. 275, pp. 18946-18961.
Carroll, et al., Proceedings of the National Academy of Sciences of the United States of America 101, 8461, 2004.
Neitz et al., Visual Neuroscience 21, 205, 2004.
Crognale et al., Visual Neuroscience 21, 197, 2004.
Winderickx et al., Nature Genetics 1, 251, 1992.
Nathans et al., Science 245, 831, 1989.
Mizrahi-Meissonnier, et al, Investigative Ophthalmology and Visual Science, 2010.
Nathans, et al. Science 232, 203, 1986.
Drummond-Borg, et al., Proceedings of the National Academy of Sciences of the United States of America 86983, 1989.
Verrelli, et al., American Journal of Human Genetics 75, 363, 2004.
Carroll, et al., Journal of Vision 2, 531, 2002.
Hofer, et al., Journal of Neuroscience 25, 9669, 2005.
Carroll, et al., Journal of the Optical Society of America A 17,499, 2000.
McMahon, et al., Journal of Vision, 8, 1, 2008.
Twelker et al., Optometry and Vision Science 86, 918, 2009.
Carkeet, et al. Optometry and Vision Science 81, 829, 2004.
Gwiazda et al., Investigative Ophthalmology & Visual Science 44, 1492, 2003.
Carroll et al., Proceedings of the National Academy of Sciences of the United States of America 106, 20948, 2009.
Neitz, et al., Color Research & Application 26, S239, 2001.
ISR and Written Opinion for PCT/US2012/021185 dated Aug. 22, 2012.
Winderickx, et al. (1993) "Haplotype diversity in the human red and green opsin genes: evidence for frequent sequence exchange in exon 3," Human Molecular Genetics, 2(9):1413-1421.

(Continued)

*Primary Examiner* — Carla J Myers
(74) *Attorney, Agent, or Firm* — McDonnell Boehnen Hulbert & Berghoff LLP

(57) ABSTRACT

The invention provides to methods for diagnosing eye-length related disorders, including myopia. The invention also provides methods for treating and limiting eye-length related disorders, including myopia. In addition, the invention provides certain haplotypes associated with eye-length related disorders, including myopia and Bornholm Eye Disease.

15 Claims, 4 Drawing Sheets

(56) References Cited

OTHER PUBLICATIONS

Michaelides, et al. (2010) "The PROM1 mutation p.R373C causes an autosomal dominant bull's eye maculopathy associated with rod, rod-cone, and macular dystrophy," IOVS, 51(9): 4771-4780.
Neitz et al., IOVS. ARVO (2011) Abstracts, Program 4896, Poster #A229.
Hahner et al., International Congress Series (2003), vol. 1239, pp. 11-16.
Hirschhorn et al., Genetics in Medicine (2002) vol. 4(2), pp. 45-61.
Hattersley et al., The Lancet. (2005) vol. 366, pp. 1315-1323.
Lucentini et al., The Scientist (2004) vol. 18, p. 20.
Halushka et al., Nature (Jul. 1999) vol. 22, pp. 239-247.
GenCard for the OPN1LW gene available via url: <genecards.org/cgi-bin/carddisp.pl?gene=OPN1LW>, printed on Feb. 19, 2014.
GeneCard for the OPN1MW gene available via url: <genecards.org/cgi-bin/carddisp.pl?gene=OPN1MW>, printed on Feb. 19, 2014.
National Center for Biotechnology Information , National Library of Medicine (Bethesda, MD, USA), NCBI SNP Database printout for the OPN1LW gene, printed on Feb. 20, 2014.
National Center for Biotechnology Information, National Library of Medicine (Bethesda, MD, USA), NCBI SNP Database printout for the OPN1MW Gene, printed on Feb. 20, 2014.
Terri L. Young, et al., (2001) "Further refinement of the MYP2 locus for autosomal dominant high myopia by linkage disequilibrium analysis", Ophthalmic Genetics, vol. 22, pp. 69-75.
Hendrik P.N. Scholl, et al., {2006) "Progressive cone dystrophy with deutan genotype and phenotype", Graefe's Arch Clin Exp Ophthalmol, vol. 244, pp. 183-191.
Hendrik P.N. Scholl, et al., {2001) "Macular dystrophy with prolan genotype and phenotype studied with cone type specific ERGs" Current Eye Research, vol. 22(3) pp. 221-228.
Sanae Oda, et al. {2003) "Analysis of L-cone/M-cone visual pigment gene arrays in females by long-range PCR" Vision Research, vol. 43, pp. 489-495.
Ahern, H. The Scientist. Jul. 1995. 9(15): 20-25.
Applied Biosystems. Product Bulletin. Automated DNA Sequencing. ABI PRISM® BigDyeTM Primer Sequencing Kit. 2000. available via uri: <tools.thermofisher.com/content/sfs/brochures/cms_040730.pdf>).
NCB I Database GenBank Accession No. NM 020061. Nov. 1, 2009. National Center for Biotechnology Information, National Library of Medicine, Bethesda, MD, USA).
NCBI Database GenBank Accession No. NM 000513. Nov. 1, 2009. National Center for Biotechnology Information, National Library of Medicine, Bethesda, MD, USA).
Hysi, et al. "A genome-wide association study for myopia and refractive error identifies a susceptibility locus at 15q25," Nat Genet, 42(10): 902-905. Oct. 2010.

* cited by examiner

METHODS FOR DIAGNOSING AND TREATING EYE-LENGTH RELATED DISORDERS

CROSS REFERENCE

This application is a continuation of U.S. application Ser. No. 14/581,116 filed Dec. 23, 2014, which is a continuation of U.S. application Ser. No. 13/349,877 filed Jan. 13, 2012, which claims priority to U.S. Provisional Patent Application Ser. No. 61/432,984 filed Jan. 14, 2011, incorporated by reference herein in its entirety.

STATEMENT OF U.S. GOVERNMENT SUPPORT

This work was supported by the National Institutes of Health grants R01EY09620, P30 FY01931, and P30EY01730. The U.S. government has certain rights in the invention.

FIELD OF THE INVENTION

The invention relates to methods for detecting and treating eye-length related disorders, including myopia. In addition, the invention relates to certain haplotypes associated with eye-length related disorders.

BACKGROUND

In a process termed emmetropization, the growth of eye length is regulated by visual experience to match the eye's optics and to compensate for genetic variation in corneal/lens curvature and power. High acuity photopic vision and, thus, the signals that guide emmetropization are initiated by light absorption photopigments found in the long wavelength (L) and middle-wavelength (M) sensitive cone photoreceptors. Changes in the pattern of light and dark in the retinal image that characterize blurred versus sharply focused images are monitored by a biological process to stop eye growth when the correct length for coordinated plano (neutral) optics is reached. However, in myopic individuals, the relative axial length of the eye to overall eye size continues to increase during development, past a length that provides near-optimal focusing of distant objects, leading to increasingly pronounced myopia.

The rate of incidence of myopia is increasing at alarming rates in many regions of the world. Until recently excessive reading during childhood was believed to be the only identifiable environmental or behavioral factor linked to the occurrence of myopia, although genetic factors were suspected. Limiting reading (and encouraging more outdoor activity) are presently the only practical techniques for preventing excessive eye lengthening in children, and corrective lenses, including glasses and contact lenses, represent the primary means for ameliorating eye-length related disorders, including myopia. While these measures optically correct the refractive errors associated with eye-length related disorders they do not address the underlying cause which is excessive growth of eye length.

Thus, there remains a need for methods of detecting a susceptibility to an eye-length related disorder, and treatments for such individuals that would prevent excessive eye lengthening.

SUMMARY OF THE INVENTION

The invention provides a method for determining the myopic potential of a patient comprising: testing a biological sample obtained from the patient to determine the L:M opsin gene haplotype of the patient; and correlating the haplotype with a predicted spherical equivalent refraction. In another aspect, the method further comprises the steps of: determining the L:M cone ratio in an eye of the patient; and correlating the L:M opsin gene haplotype and the L:M cone ratio with a predicted spherical equivalent refraction.

The invention also provides a method for diagnosing susceptibility of a patient to an eye-length related disorder, the method comprising: testing a biological sample obtained from the patient to determine the L:M opsin gene haplotype of the patient; and correlating the haplotype with a predicted spherical equivalent refraction; wherein the patient is susceptible to an eye-length related disorder if the predicted spherical equivalent refractive error (measured in diopters) has a negative power. In one aspect, the method further comprises the steps of: determining the L:M cone ratio in an eye of the patient; and correlating the L:M opsin gene haplotype and the L:M cone ratio with a predicted spherical equivalent refraction.

The invention further provides a method for diagnosing susceptibility of a patient to an eye-length related disorder, the method comprising testing a biological sample obtained from a patient for a particular combination of amino acids encoded by the patient's L opsin gene or M opsin gene, wherein the patient is susceptible to an eye-length related disorder if one of the amino acid combinations shown in Table 1 is present.

In addition, the invention provides a method of treating an eye-length related disorder comprising: testing a biological sample obtained from the patient to determine the L:M opsin gene haplotype of the patient; determining the L:M cone ratio in an eye of the patient; correlating the haplotype and the L:M cone ratio with a predicted spherical equivalent refraction; providing the patient with a therapeutic device comprising a wavelength-dependent filter if the patient's predicted spherical equivalent refractive error has a negative, power.

In one aspect, the wavelengths filtered by the wavelength-dependent filter are selected based on the L:M opsin gene haplotype and the L:M cone ratio of the patient.

In another aspect, a therapeutic device used in a method of the invention is a pair of spectacles comprising blur-inducing lenses. In certain aspects, the blur-inducing lenses induce blurring by one or more of: small bumps or depressions in one or both surfaces of the lenses; inclusions within the lenses of a material different from the lens material; incorporation of higher-level aberrations in the lenses; providing an increased correlation between the activities of neighboring cone photoreceptors by one or both lenses; and coatings or films applied to one or both surfaces of the lenses to produce diffusive or diffractive blur.

In yet another aspect, a therapeutic device used in a method of the invention comprises blur-inducing, contact lenses. In certain aspects, the blur-inducing contact lenses induce bluffing by one or more of: inclusions within the lenses of a material different from the lens material; incorporation of higher-level aberrations in the lenses; and coatings or films applied to one or both surfaces of the lenses that produce blur by diffusion, diffraction or light scattering.

In certain aspects, the L:M opsin gene haplotype identified in a method of the invention is one of haplotypes 1 to 13 as set forth in Table 1.

The invention also provides a microarray for determining susceptibility of a patient to an eye-length related disorder comprising a set of allele specific oligonucleotides capable of identifying at least one haplotypes 1 to 13 as set forth in Table 1.

The invention further provides kits for determining whether a patient is susceptible to an eye-length related disorder. In one aspect, a kit of the invention comprises: at least one pair of oligonucleotides that can identify at least one of haplotypes 1 to 13 as set forth in Table 1; and instructions for use. In another aspect, a kit of the invention comprises an assay for detecting at least one of haplotypes 1 to 13 as set forth in Table 1.

In another aspect, the present invention provides methods for limiting introduction of refractive error in a subject's eye caused by exposure to display screens, comprising the subject wearing a therapeutic optical device that comprises a wavelength-dependent filter capable of preferentially blocking red light emanating from the display screen prior to entry into the subject's eye, thereby limiting introduction of refractive error in the subject's eye.

In a further aspect, the present invention provides methods for limiting development of an eye-length related disorder in a subject, comprising the subject wearing a therapeutic optical device that comprises a wavelength-dependent filter capable of preferentially blocking red light emanating from a display screen prior to entry into the subject's eye, thereby limiting development of an eye-length related disorder in the subject. In one embodiment, the eye-length related disorder comprises myopia.

Specific preferred embodiments of the invention will become evident from the following more detailed description of certain preferred embodiments and the claims.

DETAILED DESCRIPTION OF THE INVENTION

Figure 1:
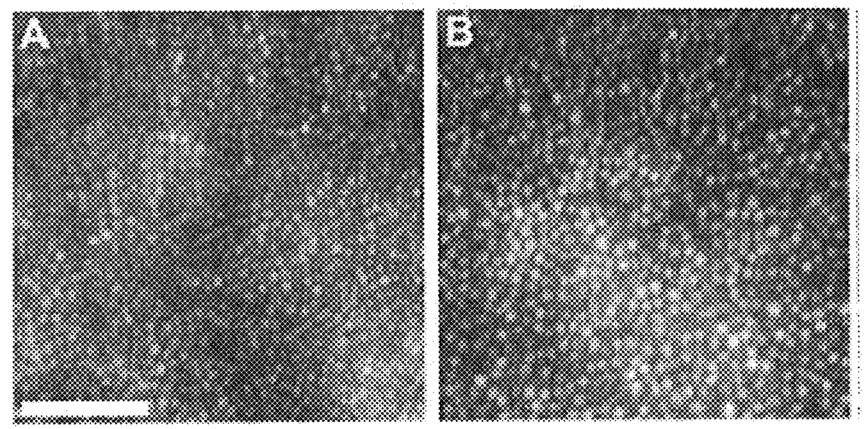
FIG. 1. Averaged, adaptive optics retinal images of the cone mosaic of participants with LIAVA variants (B, C, D) compared with a normal control (A). For subjects shown in B, C, & D cones expressing the LIAVA variant had a low reflectance compared to normal cones and appear as dark area in the mosaic. There was large variability in the proportion of cones expressing the LIAVA variant. B, C & D have low, medium and high proportions of cones expressing the myopia-genic variant which correlates with axial length (E) and also with refractive error.
Figure 1:
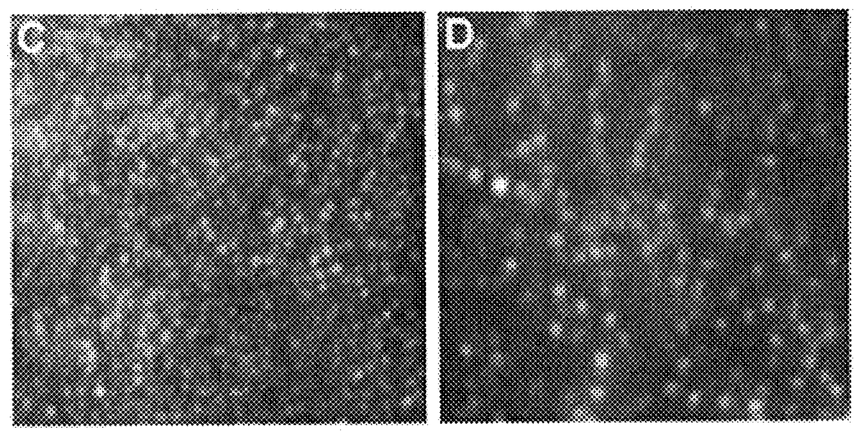
Figure 1:
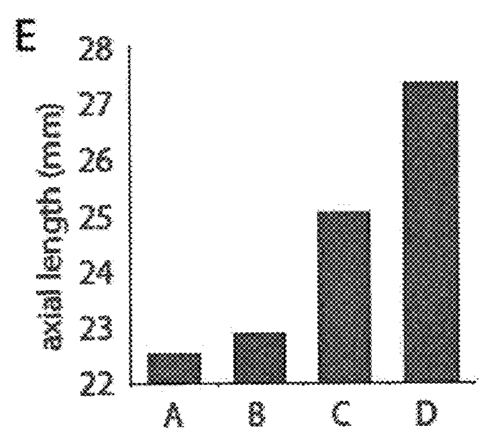

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides methods that can be used to determine the benefit of a preventative treatment for an eye-length disorder and to determine the appropriate prescription of characteristics of preventative optics for a patient who is identified as having a susceptibility to an eye-length related disorder. As discussed herein, such preventative optics include spectral characteristics and/or dispersive properties that can prevent eye-length growth, which if left uncontrolled would lead to an eye-length related disorder.

In one embodiment, the invention provides a method for diagnosing susceptibility of a patient to an eye-length related disorder, the method comprising: testing a biological sample obtained from the patient to determine the patient's L:M opsin gene haplotype, and correlating the haplotype with a predicted spherical equivalent refraction; wherein the patient is susceptible to an eye-length related disorder if the predicted spherical equivalent refraction is a negative diopter.

As used herein, the term "correlating" refers to the step of using the combination of information about a patient's cone ratio and opsin haplotype in order to determine the susceptibility of the patient to an eye-length related disorder as shown and discussed herein.

As used herein, the phrase "eye-length related disorder" includes, but is not limited to, myopia.

In one embodiment, the L:M opsin gene haplotype is determined by identifying the nucleotide sequence of a patient's DNA to determine the patient's Xq28 opsin gene locus haplotype. The haploytpe can be determined by identifying, the nucleotide sequence of exons 2, 3, and 4 of the OPN1LW and OPN1MW genes. As discussed herein, the haplotypes are created by the amino acids encoded by codons 65, 111, 116, 153, 171, 178, 180, 230, 233, and 236 of the OPN1LW and OPN1MW genes. In a particular embodiment, the haplotype is determined by the amino acids encoded by codons 153, 171, 178, and 180 in exon 3 and codon 236 in exon 4. In a preferred embodiment, the L:M opsin gene haplotype is one of the 13 haplotypes shown in Table 1, which are shown herein for the first time as being associated with myopia (see Examples and FIG. 3A). Thus, if a patient has one of the 13 haplotypes identified in Table 1, that patient is diagnosed as being susceptible to an eye-length related disorder. In particular, a patient having one of the haplotypes shown in Table 1 is diagnosed as being susceptible to myopia. In one embodiment, a patient is diagnosed as being susceptible to myopia if one of the variant amino acid combinations shown in Table 1 associated with the L-opsin gene is identified in the patient. In another embodiment, a patient is diagnosed as being susceptible to myopia if one of the variant amino acid combinations shown in Table 1 associated with the M-opsin gene is identified in the patient.

TABLE 1

Myopia Haplotypes

| | L-OPSIN Codons | | | | | M-OPSIN Codons | | | |
|---|---|---|---|---|---|---|---|---|---|
| | 153 | 171 | 178 | 180 | 236 | 153 | 171 | 178 | 180 |
| 1 | M | I | I | S | M | M | V | V | A |
| 2 | M | V | I | S | M | M | V | V | A |
| 3 | L | V | I | S | M | M | V | V | A |
| 4 | M | V | I | S | M | M | V | I | A |
| 5 | L | V | I | A | M | M | V | I | A |
| 6 | M | V | I | A | M | M | V | I | A |
| 7 | L | V | I | S | M | L/M | V | I | A |
| 8 | L | V | I | S | M | M | V | I | A |
| 9 | L | I | I | S | M | M | V | V | A |
| 10 | M | V | V | A | V | M | V | I | A |
| 11 | M | V | I | S | V | M | V | V | A |
| 12 | L | V | I | S | M | L | V | I | S |
| 13 | L | V | I | A | M | L/M | V | I | A |

In another embodiment, the invention provides a method for diagnosing susceptibility of a patient to an eye-length related disorder, the method comprising: testing a biological sample obtained from the patient to determine the patient's L:M opsin gene haplotype, determining the L:M cone ratio in an eye of the patient, and correlating the L:M opsin gene haplotype and the L:M cone ratio with a predicted spherical equivalent refraction, wherein the patient is susceptible to an eye-length related disorder if the predicted spherical equivalent refractive error is a negative power (in diopters).

The L:M cone ratio can be determined using methods known to those of skill in the art. For example, adaptive optics retinal imaging can be used as described herein, or an electroretinogram (ERG) (such as a flicker photometric ERG) and individualized cone spectra can be used. The L:M cone ratio measurement can also involve genetics, as described for example in Neitz and Neitz, J. Vis. 2:531-42, 2002. Another non-limiting example of measuring L:M cone ratio includes wide-field color multifocal ERG as described in Kuchenbecker et al., Vis. Neurosci. 25(3):301-6, 2008. Another non-limiting example of measuring L:M cone ratio includes measuring the ratio of red-to-green light perceived to have the minimum flicker using psychophysical heterochromatic flicker photometry as described in Gunther and Dobkins Vision Research 42:1367-1378, 2002.

In one embodiment, the invention provides a method for determining the myopic potential of a patient comprising testing a biological sample obtained from the patient to determine the patient's L:M opsin gene haplotype.

As used herein, the term "myopic potential" refers to the predicted spherical equivalent refraction associated with an L:M opsin haplotype, which correlates with the predicted degree of myopia that the patient has or is likely to have. In particular, the myopic potential refers to a certain spherical equivalent refraction predicted based on the patient's particular L:M opsin gene haplotype, as shown, for example, in FIG. 3A.

In a particular embodiment, myopic potential can be more specifically determined by measuring the patient's L:M cone ratio, and correlating the ratio with the spherical equivalent refraction predicted for the particular L:M opsin gene haplotype. For example, as discussed in the examples below, the L:M cone ratio can be determined for a patient that has a certain L:M opsin haplotype, such as a haplotype shown in Table 1. The L:M cone ratio is determined, and a calculation is made to arrive at the more specific predicted myopic potential. For instance, if a person had haplotype 8 (FIG. 3A), their myopic potential is −4.5 diopters. If that person had a 1:1 cone ratio they would be expected to have the full −4.5 diopters of refractive error. However, if he had nearly 100 percent L cones he would be expected to be nearly emmetropic. 75% L cones falls midway between a 1:1 cone ratio (50% L) and 100% L so a person with haplotype 8 and 75% L cones would be predicted to have 50% of the SER (or −4.5/2=−2.25 diopters).

As used herein, the phrase "susceptibility to an eye-length related disorder" refers to the high likelihood of developing an eye-length related disorder, such as myopia, when a certain L:M opsin gene haplotype is present. In one embodiment, a patient is considered susceptible to an eye-length related disorder if one of the haplotypes shown in Table 1 is present, which are listed in order of increasing myopic potential.

After identifying a patient that is susceptible to an eye-length related disorder and/or has a myopic potential associated with a negative diopter as described herein, an eye care provider can prescribe a treatment protocol and/or suggest certain behaviors intended to treat or reduce the myopic potential of the patient. For example, a patient may be treated with a therapeutic device (as described herein, for example) or be given pharmacological intervention. In addition or instead of such treatments, a patient may be told to limit exposure to red light or green light (depending on the patient's particular variants) limit reading at a young age and spending more time doing activities outdoors.

The term "biological sample" as used herein includes, but is not limited to, blood, saliva, cells from buccal swabbing, biopsies of skin, amniotic fluid, various other tissues and the like. Methods for purifying or partially purifying nucleic acids from a biological sample for use in diagnostic assays are well known in the art. The nucleic, acid can be, for example, genomic DNA, RNA, or cDNA. Genomic DNA can be isolated, for example, from peripheral blood leukocytes using QIAamp DNA Blood Maxi Kits (Qiagen, Valencia, Calif.).

In another embodiment, the invention provides a method for diagnosing Bornholm Eye Disease (BED) in a patient, the method comprising obtaining a biological sample from the patient and identifying the nucleotide sequence of the patient's L and M opsin genes, wherein the patient is diagnosed as having BED if the patient has a normal opsin gene and a variant opsin gene. In a preferred embodiment, the variant opsin gene comprises Leucine at amino acid position 153 (L153), Valine at position 171 (V171), Alanine at 174 (A174), Valine at 178 (V178), and Alanine at 180 (A180) ("LVAVA") or Leucine at amino acid position 153 (L153), Isoleucine at position 171 (I171), Alanine at 174 (A174), Valine at 178 (V178), and Alanine at 180 (A180) ("LIAVA") in either the L or M opsin gene. In another embodiment, the second gene has the combination of Methionine, Valine, Valine, Valine, and Alanine at amino acids at positions 153, 171, 174, 178, and 180 ("MVVVA").

The diagnostic methods of the invention involve the use of standard molecular biology methods, including in one non-limiting embodiment the polymerase chain reaction (PCR), to determine the L:M opsin gene haplotype of a patient. There are currently a variety of molecular biological methods available that allow examination of the DNA sequences of the L and M opsin genes. For example, gene fragments may be amplified using the polymerase chain reaction (PCR). The genes can be separately and selectively amplified as described previously (Neitz et al., Vision Research 35: 2395-2407, 1995).

Amplified gene fragments will preferably be subjected to one or more of the following procedures that provide information about the DNA sequence:

1) Direct DNA sequence of the PCR products as described previously (J. Neitz, M. Neitz and Grishok, supra, 1995).

2) Restriction digestion analysis (described previously in J. Neitz, M. Neitz and Grishok, supra, 1995).

3) Single strand conformation polymorphism or other similar procedures. The amplified DNA fragment is fluorescently or radioactively end labeled, denatured into single strands, and the strands are separated electrophoretically. Based on the mobility of the strands in the electric field, information about the DNA sequence can be deduced.

In another embodiment, the invention provides a method of treating an eye-length related disorder comprising: testing a biological sample obtained from a patient to determine the L:M opsin gene haplotype of the patient; determining the L:M cone ratio in an eye of the patient; correlating the haplotype and the L:M cone ratio with a predicted spherical equivalent refraction; providing the patient with a therapeutic device comprising a wavelength-dependent filter if the patient's predicted spherical equivalent refraction is a negative diopter. In one embodiment, the opsin gene haplotype is one of haplotypes 1 to 13 as set forth in Table 1.

As discussed in International Patent Application Publication No. WO 2010/075319, the entire contents of which are hereby incorporated by reference in their entirety, genetic variation in opsin genes affects the absorbance characteristics of the opsin photoreceptor protein. Thus, the wavelength-dependent filter utilized in a method of the invention is intended to filter light prior to entry into the eye in order to adjust the effective absorbance spectrum of variant opsin photoreceptor proteins. In patients having a defective M photoreceptor protein, caused by a variant M-opsin gene, that absorbs less light than the normal M photoreceptor protein, the wavelength-dependent filter may preferentially block red light. On the other hand, in patients having a defective L photoreceptor protein, caused by a variant M-opsin gene, that absorbs less light than the normal L photoreceptor protein, the wavelength-dependent filter may preferentially block green light.

In certain embodiments, the particular wavelength-dependent filter utilized in a method of the invention can be selected based on the patient's L:M opsin gene haplotype, which identifies specific photoreceptor variants and/or the patient's L:M cone ratio, which identifies the number of L photoreceptors relative M photoreceptors present in the patient's eye. Based on the particular L:M opsin gene haplotype and/or the L:M ratio, a filter can be designed to block and/or transmit very specific wavelengths to restore relative absorption characteristics of the defective photoreceptor proteins. Thus, the invention further provides methods for customizing a therapeutic device for a particular patient based on the L:M opsin gene haplotype and/or the L:M cone ratio of the patient. For example, if the patient had opsin variants associated with more active red (M) cones, the filter could be designed to block red light; whereas if the patient had opsin variants associated with more active green (L) cones, the filter could be designed to block green light.

In certain embodiments, the therapeutic device comprises blur-inducing lenses, for example as described in International Patent Application Publication No. WO 2010/075319. In one embodiment, the device is a pair of spectacles comprising blur-inducing lenses, where the blur is designed to reduce the relative activities between neighboring cone photoreceptors in the retina which has been shown herein to result in signals that stimulate the eye to grow in length abnormally. The blur-inducing lenses can be made to induce blurring, for example, by one or more of: small bumps or depressions in one or both surfaces of the lenses; inclusions within the lenses of a material different from the lens material; incorporation of higher-level aberrations in the lenses; and coatings or films that induce blur by light scatter, diffusion or diffraction applied to one or both surfaces of the lenses.

In yet another embodiment, the therapeutic device comprises blur-inducing contact lenses. The blur-inducing, contact lenses can be made to induce blurring, for example, by one or more of inclusions within the lenses of a material different from the lens material; incorporation of higher-level aberrations in the lenses; providing progressive negative corrections in one or both lenses from the center of the lens to the bottom of the lenses; and coatings or films that induce blur by light scatter, diffusion or diffraction applied to one or both surfaces of the lenses.

In one further aspect, the present invention provides methods for limiting introduction of refractive error in a subject's eye caused by exposure to display screens, comprising the subject wearing a therapeutic, optical device that comprises a wavelength-dependent filter capable of preferentially blocking red light emanating from the display screen prior to entry into the subject's eye, thereby limiting introduction of refractive error, in the subject's eye.

In a still further aspect, the present invention, provides methods for limiting development of an eye-length related disorder in a subject, comprising the subject wearing a therapeutic optical device that comprises a wavelength-dependent filter capable of preferentially blocking red light emanating from a display screen prior to entry into the subject's eye, thereby limiting development of an eye-length related disorder in the subject. In one embodiment, the eye-length related disorder comprises myopia.

These methods can be used to limit damage to the eye caused by excessive exposure to red-light from a screen display. In various non-limiting embodiments, the screen display may be a computer monitor, a tablet monitor, a television screen, a handheld device screen, a video game screen, a head-mounted display screen, and a movie theater screen.

As used herein, "limiting" means one or more of (a) reducing the incidence of introduction of refractive error in a subject's eye and/or reducing the incidence of eye-length related disorders developing in treated subjects: (b) reducing the severity of subsequently developed refractive error in a subject's eye and/or reducing the severity of a subsequently developed eye-length related disorder in the subject; and/or (c) limiting or preventing development of symptoms characteristic of refractive error in a subject's eye and/or an eye-length related disorder.

In each of these further aspects, the therapeutic optical device may further comprise a blur-inducing lens, including but not limited to those disclosed, in WO 2010/075319 and as disclosed above. In one embodiment, the blur-inducing lens comprises a holographic diffuser applied to the lens surface, for example, as described in the examples below. The holographic diffuser can be used, for example, to spread the incident light rays from the display over a desired angle to produce a slight blur and thus reduce activity differences between adjacent cones. In any of these embodiments, the therapeutic optical device may be of any suitable type, including but not limited to glasses/spectacles and contact lenses.

Any suitable subject may be treated in these aspects, including children 21 years of age or Younger, preferably between the ages of 3-21, 3-20, 3-19, or 3-18. In another embodiment that can be combined with any of the above embodiments, wherein the subject is susceptible to an eye-length related disorder, such as myopia. This embodiment may comprise treating any subject at risk as discussed in any of the preceding disclosure. In one particular embodiment, the subject is susceptible to an eye-length related disorder if the subject has an L:M opsin gene haplotype as set forth in Table 1.

In one embodiment, the invention provides kits that can be used, for example, for eye-length related disorder diagnosis. In certain embodiments, a kit of the invention comprises a set of haplotype specific oligonucleotides to identify the presence or absence of L:M opsin gene haplotypes, such as those identified in Table 1. For example, a kit comprises: a set of primer pairs for amplifying portions of exons 3 and 4 associated with the haplotypes described herein, such as 1, 2, 3, 4, 5, 6, 7, 8, 9, 10, 11, 12, or 13 of the haplotypes listed in Table 1; a set of probes that can hybridize to portions of exons 3 and 4 associated with the haplotypes described herein; and/or a microarray, such as a SNP chip. Primers and probes can be readily and easily designed by those skilled in the art by reference to a sequence associated with the portions of exons 3 and 4 associated with the haplotypes described herein. Microarrays can also be easily and readily designed with oligonucleotides of the invention that correspond to the portions of exons 3 and 4 associated with the haplotypes described herein. Alternatively, analysis could be done using a mass spectrometry instrument (for example, a MassArray™ instrument) that allows genotyping at known polymorphic sites using specially designed PCR primers followed by mass spectrometry. This technique is suited to diagnosis of conditions such as axial length disorders described here whose genetic underpinnings are well understood. A MassArray™ primer extension process detects sequence differences at the single nucleotide level. An initial round of PCR amplifies from genomic DNA a short length of DNA surrounding the SNP. This is followed by single-base extensions of a primer that anneals directly adjacent to the SNP. The primer is extended dependent upon the template sequence, resulting in an allele-specific difference in mass between extension products. This mass difference allows differentiation between SNP alleles using MALDI TOF mass spectrometry.

In another embodiment, the invention provides a mouse model of an eye-length related disorder as described in the Examples herein, which Comprises a variant green (L) photopigment protein associated with myopia. The invention further provides a mouse model that expresses variant red (M) and normal or variant green (L) photopigment proteins, wherein a variant protein has an amino acid sequence associated with myopia. Such mice can be generated as described, for example, in the Methods provided herein. Such mice have been generated using the method described herein, wherein the heterozygous mice of the method comprise the red and green photopigment proteins. In certain embodiments, a mouse model of the invention can be used to test eye-length related disorder intervention, such as pharmacological or genetic intervention.

In certain embodiments, the present invention provides a machine readable storage medium, comprising a set of instructions for causing a diagnostic device to measure a patient's L:M cone ratio or L:M opsin gene haplotype. In other embodiments, the invention provides a machine readable storage medium that comprises instructions for causing a processor to execute automated method steps for correlating a patient's L:M opsin gene haplotype and L:M cone ratio to determine an appropriate prescription of characteristics of preventative optics for a patient who is identified as having a susceptibility to an eye-length related disorder. As used herein the term "computer readable storage medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system. As used herein, "diagnostic device" means a device capable of carrying out the L:M cone ratio measurements or L:M opsin gene haplotype determination to carry out the methods of invention, including but not limited to a microarray reader or a mass spectrometer.

The references cited herein, to the extent that they provide exemplary procedural or other details supplementary to those set forth herein, are specifically incorporated by reference.

Those of skill in the art, in light, of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

EXAMPLES

The following examples, including the experiments conducted and results achieved are provided for illustrative purposes only and are not to be construed as limiting the invention.

Example 1

Mutant OPN1LW and OPN1MW Genes in Bornholm Eye Disease

The first identified Yid-grade myopia locus was localized to chromosome Xq2.8 and designated MYP1 (M. Schwartz, M. Haim, D. Skarsholm, *Clinical Genetics* 38, 281 (October, 1990)), The phenotype is also known as the Bornholm Eye Disease (BED), and is an X-linked cone dysfunction syndrome with myopia, astigmatism and optic nerve changes (T. L. Young et al. *Archives of Ophthalmology* 122, 897 (June, 2004); U, Radhakrishna et al., *Investigative Ophthalmology & Visual Science* supplement (abstract #3814) (2005); Michaelides et al., *Ophthalmology* 112, 1448 (2005)). Part of the phenotype of BED with X-linked cone dysfunction syndrome is an abnormal cone electroretinogram (ERG). The OPN1LW and OPN1MW genes reside at Xq28 and encode cone photopigments responsible for the initial events that generate the cone ERG.

The L and M Cone opsin genes were evaluated as candidates for the BED phenotype. The two unrelated X-linked myopia/cone dysfunction families described by Young et al. (T. L. Young et al., *Archives of Ophthalmology* 122, 897 (June, 2004)) have color vision deficiencies which are caused by the absence of an OPN1MW gene in either of the first two positions in the cone opsin gene array in the original BED (M. Schwartz, M. Haim, D. Skarsholm, *Clinical Genetics* 38, 281 (October, 1990)) family and by the absence of an intact OPN1LW gene in the case of the Minnesota (MN) family. In a third family, residing in India, the affected males (U. Radhakrishna et al., *Investigative Ophthalmology & Visual Science* supplement (abstract #3814) (2005)) have normal color vision. The first gene in the X-chromosome opsin array was selectively amplified and individual exons from affected and unaffected males in the MN, BED1, and Indian families were directly sequenced. The opsin genes downstream of the first gene were also selectively amplified, and the exons were directly sequenced. For all affected males in the MN family, the first position (5'-most) opsin gene in the array encoded an M opsin with an unusual combination of amino acids specified by the dimorphic codons in exon 3. This combination was Leucine at amino acid position 153 (L153), Valine at position 171 (V171), Alanine at 174 (A174), Valine at 178 (V178), and Alanine at 180 (A180), henceforth abbreviated “LVAVA.” The second gene in the array encoded a combination of amino acids at these positions (“MVVVA”) typically found in M opsins in individuals with no vision abnormalities.

The affected members of the second, unrelated BED family (BED1) reported by Young et al. (T. L. Young et al., *Archives of Ophthalmology* 122, 897 (June, 2004)) and the Indian family (U. Radhakrishna et al., *Investigative Ophthalmology & Visual Science* supplement (abstract #3814) (2005)) were also found to have the LVAVA combination, but in the L opsin. In both of these latter families, the downstream genes in affected males encoded variants that are typical of individuals with normal vision. Unaffected males in the BED families did not have an LVAVA variant. As a control experiment, 261 OPN1MW genes and 320 OPN1LW from males with no serious vision abnormality were sequenced. None of the genes specified the LVAVA combination.

Affected males in five additional families (M. Michaelides et al., *Ophthalmology* 112, 1448 (2005); M. McClements, M. Neitz, A. Moore, D. M. Hunt, *Invest Ophthalmol Vis Sci*, ARVO E (2010)) and one other unrelated individual with the BED phenotype were found to have either the LVAVA combination or a similar combination, in which isoleucine is present at position 171 (I171) instead of valine. This combination is designated “LIAVA” and was previously shown to cause photoreceptors to be non-functional in adults (J. Carroll, M. Neitz, H. Hofer, J. Neitz, D. R. Williams, *Proceedings of the National Academy of Sciences of the United States of America* 101, 8461 (2004), Neitz et al., *Visual Neuroscience* 21, 205 (2004); M. A. Crognale et al., *Visual Neuroscience* 21, 197 (2004)). Affected members of a seventh family reported to have X-linked cone dysfunction syndrome were found to have a mutation that replaces the cysteine normally found at position 203 with arginine (C203R) in both the L and M opsins (M. Michaelides et al., *Ophthalmology* 112, 1448 (2005)), a mutation known to render the opsin non-functional (M. Michaelides et al., *Ophthalmology* 112, 1448 (2005); J. Winderickx et al., *Nature Genetics* 1, 251 (1992); Nathans et al., *Science* 245, 831 (1989)).

Cone Phenotype of BED Opsin Mutation in Mice with a Targeted Gene Replacement

Although the LIAVA and C203R mutations found in some of the families have been previously documented to cause cone photoreceptor malfunction, the LVAVA amino acid combination found in many BED families and its impact on cone function and viability was never identified. Individuals with LVAVA encoded in their only expressed X-linked cone pigment gene have cone dystrophy indicating that cones expressing this haplotype function abnormally and eventually degenerate. To verify the abnormal cone function associated with LVAVA, a mouse line was created in which exons 2 through 6 of the mouse M opsin gene were replaced with a cDNA containing exons 2-6 of a human L opsin gene that specified the LVAVA combination. A control mouse line was also created that was identical in the structure of the X-chromosome opsin gene replacement except that it specified the combination LIAIS, which is commonly found in individuals with normal vision. The mice were tested using ON-OFF ERG using an L cone isolating stimulus. The ERG amplitudes were reduced in mice with the LVAVA mutation compared to control mice, consistent with the abnormal ERG findings in the BED patients (T. L. Young et al., *Archives of Ophthalmology* 122, 897 (June, 2004)). The ERG-a-wave, the component most associated with photoreceptor function, was reduced in amplitude by half in the LVAVA mouse compared to the control mouse.

Cone Ratio and the Severity of the BED Phenotype

In the case of individuals with the LIAVA or C203R mutation, both of which render cones expressing them non-functional, a single cone type absorbing in the middle-to-long wavelengths is left, accounting for their color vision defects. In the case of individuals with the LVAVA mutations and a color vision defect, cones containing the LVAVA opsin function, but the first two genes in array encode the same opsin type, L for the BED1 family, and M for the MN family. In contrast, in the Indian family, L cones express the abnormally functioning LVAVA photopigments, but a normal M opsin is expressed in a separate cone subpopulation and the individuals with BED myopia in this family have normal color vision.

Usually, only the first two genes in the X-chromosome opsin gene array are expressed. However, the BED/X-linked high myopia patients have one X-linked opsin gene with a mutation that causes cone photoreceptor malfunction and second normal gene. Each of the first two opsin genes from the array is expressed in its own submosaic of cones with the two being randomly interspersed. Each of the mutations found to be associated with BED/X-linked high myopia produces a more debilitating vision disorder (cone dystrophy in the cases of LVAVA) or one in which L and M cone function is absent entirely in adults (blue cone monochromacy in the case of LIAVA and C203R) when it is the only L/M opsin expressed in an individual's retina. What appears to rescue the high myopia patients from the more debilitating retinal phenotype is the presence of a normal X-chromosome pigment gene expressed in a submosaic of cones. However, having the interspersed normal and mutant cones appears to be responsible for the high myopia.

There is widespread variability in L:M cone ratio in the normal population. A similar variation in cone ratio was found among the LIAVA BED subjects (FIG. 1). It is clear from the adaptive optics (AO) images that the mutations associated with BED disrupt the cone mosaic, most likely impairing the ability of the eye to extract reliable information about the presence of sharply focused, fine-grained images from comparisons of activity among neighboring cones and thus interferes with emmetropization. Imaging of three individuals showed a dramatic illustration of how the degree of cone mosaic disruption correlated with axial length and the severity of myopia (FIG. 1E).

In the LVAVA BED patients, the mutant cones are functional, but the difference in response between normal and mutant cones is larger than would be produced by two normal cones, one on the light side and one on the dark side of a sharply focused dark-light edge in an image. In adulthood, cones containing an opsin with the LIAVA combination are completely non-functional (J. Carroll, M. Neitz, H. Hofer, J, Neitz, R. Williams, *Proceedings of the National Academy of Sciences of the United States of America* 101, 8461 (2004); M. Neitz et al., *Visual Neuroscience* 21, 205 (2004; M. A. Crognale et al., *Visual Neuroscience* 21, 197 (2004); however, there is evidence that they function to some degree in childhood (L. Mizrahi-Meissonnier, S. Merin, E. Banin, D. Sharon, *Investigative Ophthalmology and Visual Science* (Mar. 20, 2010, 2010)).

Here, for the first time, the complete etiology for a form of myopia (i.e., Bornholm Eye Disease) was determined.

Example 2

Opsin Mutations and Haylotypes Associated with Myopia

Among humans with normal color vision there is tremendous variation in the amino acid sequences of the L and M opsins that has arisen via unequal homologous recombination (J. Nathans, T. P. Piantanida, R. L. Eddy. T. B. Shows. D. S. Hogness, *Science* 232, 203 (1986); M. Drummond-Born, S. S. Deeb A. G. Motulsky, *Proceedings of the National Academy of Sciences of the Untied States of America* 86, 983 (1989); B. C. Verrelli, S. A. Tishkoff, *American Journal of Human Genetics* 75, 363 (2004)). For example, in the control sample described above, there were 34 different L opsin sequences in 320 subjects, and 17 different M opsin sequences in 261 subjects. The ratio of L to M cones also varies widely among humans. For example, among Caucasian males with normal color vision, the ratio of L:M cones ranges hum 1.1:1 to 19:1, with an average of 2.7:1 (J. Carroll, M. Neitz, J. Neitz, *Journal of Vision* 2, 531 (2002); H. Hofer, J. Carroll, J. Neitz, M. Neitz, D. R. Williams, *Journal of Neuroscience* 25, 9669 (October, 2005)).

Figure 2:
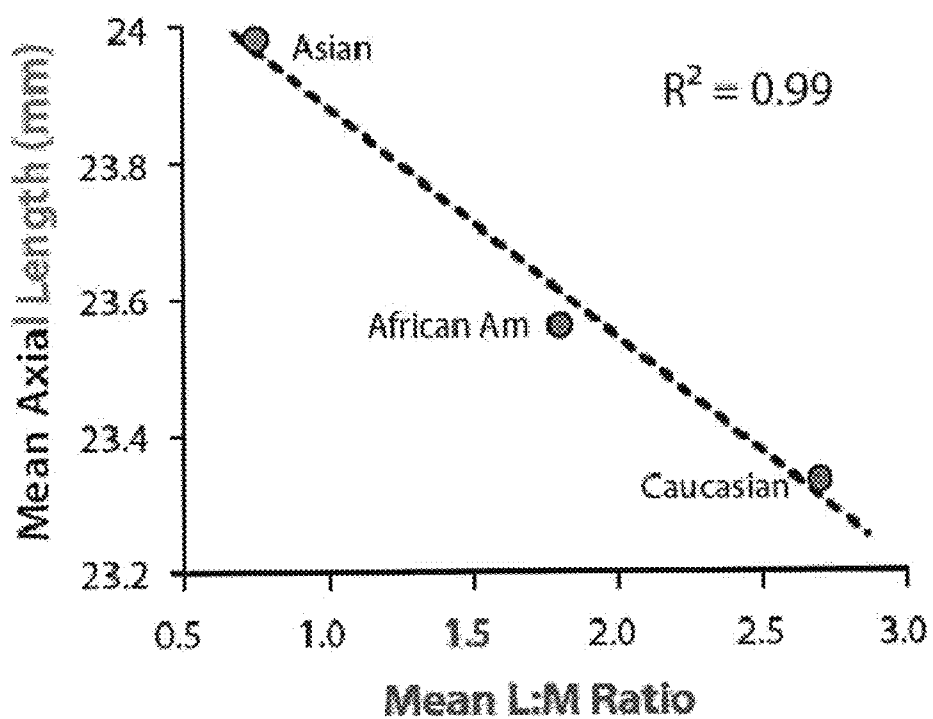
FIG. 2. Association between axial length and cone ratio for different ethnic groups. There was a high positive correlation between L:M cone ratio and axial length (and incidence of myopia) across ethnic groups.

To determine if a biased L:M cone ratio would be protective against myopia, the mean axial length versus the mean L:M cone ratios for three ethnic groups were plotted. L:M cone ratios were estimated previously from ERGs and genetics for males self-reported to be Caucasian (n=86) (H. Hofer, J. Carroll, J. Neitz, M. Neitz, D. R. Williams, *Journal of Neuroscience* 25, 9669 (October, 2005); J. Carroll, C. McMahon, M. Neitz, J. Neitz, *Journal of the Optical Society of America A* 17, 499 (March, 2000)) and African (n=28) (C. McMahon, J. Carroll, S. Awua, J. Neitz, M. Neitz, *Journal of Vision* 8, 1 (2008)). The L:M ratio for a sample of 5 unrelated Japanese males (n=5) was also determined. The values ranged from 48.13% L to 38% L cones, with an average of 43.4% L cones corresponding to a mean ratio of 0.8 L:1M. Even for this small sample the results indicated a statistically significant difference ($p<0.0001$; Mann Whitney U) in the mean L:M cone ratio for Caucasian males versus Japanese males (FIG. 2). The mean axial length data were from Twelker et al. (J. D. Twelker et al., *Optometry and Vision Science* 86, 918 (2009)) for boys age 12 at their last birthday in the ethnic categories White, African American, and Asian. The L:M cone ratio bias was strongly negatively associated with axial length ($R^2=0.99$), and thus with susceptibility to myopia.

Variation in the coding sequences of the OPN1LW and OPN1MW genes was then evaluated as candidates for causing myopia. Subjects were 336 self-reported Caucasian males, age 21 years or older, all of whom were confirmed to have normal color vision. Axial lengths and conical curvatures were measured using the Zeiss IOL master without cycloplegia, and their spherical equivalent refraction (SER) were calculated using an equation described in Methods below. An opsin gene haplotype was determined for each subject by selectively amplifying and sequencing exons 2, 3 and 4 of the OPN1LW and OPN1MW genes. Haplotypes were created using the amino acids encoded by codons 65, 111, 116, 153, 171, 178, 180, 230, 233, and 236 of the OPN1LW and OPN1MW genes. Complete haplotypes were obtained for 303 subjects. Haplotypes were identified as the combination of amino acids at the variant positions encoded by exons 2, 3 and 4. Over 50%, or 159 males, belonged to 13 haplotype groups with at least 3 subjects per group (see FIG. 3A). Within each of the 13 haplotype groups there was no variation at codons 65, 111, 116, 230, or 233 in either gene or in codon 236 in OPN1MW genes.

Figure 3:
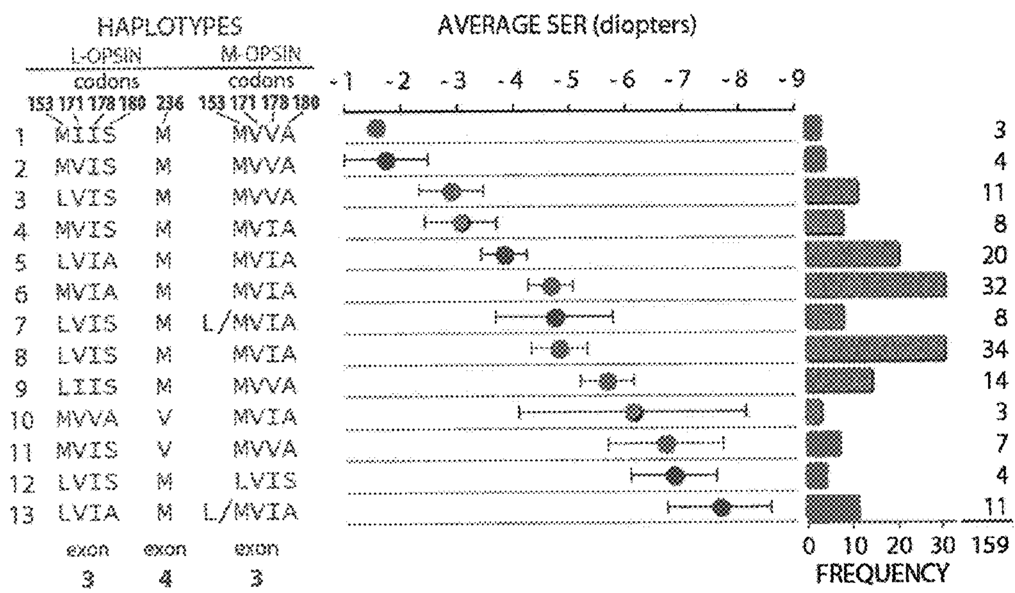
FIG. 3. (A) Myopic potential of 13 different UM photopigment haplotypes, from 159 males, arranged in order of increasing myopic potential. The number of individuals with each haplotype is given at the right. Haplotype designations use the single letter amino acid code: M=methionine, 1=isoleucine, S=serine, V=valine, A=alanine, and L=leucine. Average SER is the mean spherical equivalent refraction calculated for the most myopic half of the subjects for each haplotype, ±1 SEM. (B) Predicted versus observed spherical equivalent refraction (SER) for 11 subjects with haplotypes corresponding to those described in (A). The L:M cone ratio was estimated for each subject and is expressed as the percentage of L plus M cones that are L.
Figure 3:
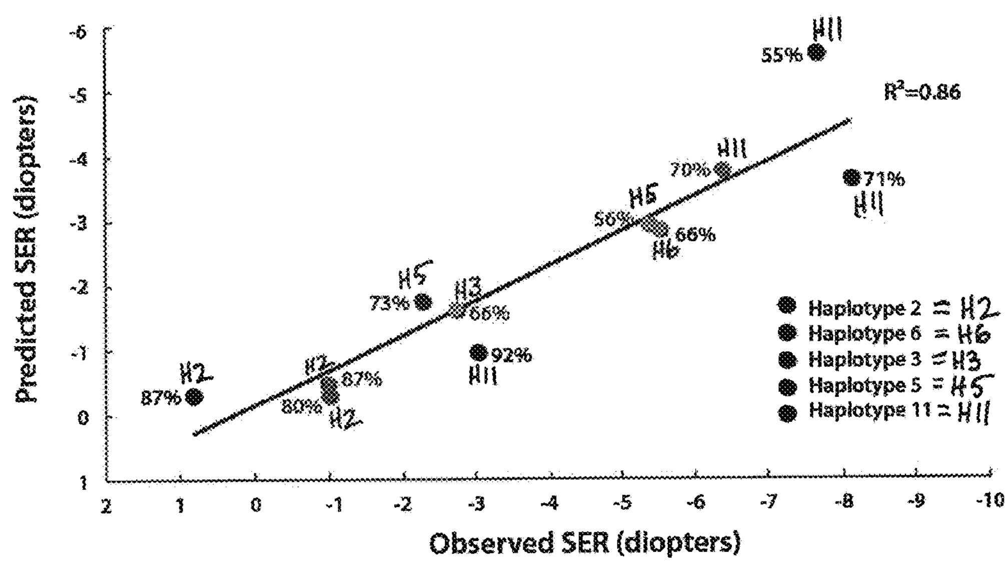

Within each haplotype, it was expected that subjects varied in cone ratio, and subjects with a highly biased L:M cone ratio would be protected from the myopia-genic action of the haplotype. The average SER for each haplotype was calculated as the mean SER for the most myopic half of the subjects within the haplotype. The most-myopic 50% from each group were considered, based on the premise that these individuals would have more nearly equal L:M cone ratios and be a more accurate reflection of potential for each haplotype to cause myopia. The haplotypes were arranged in order of myopic potential with haplotype number 1 having the least potential for causing myopia, and haplotype number 13 having the greatest, and the myopic potential increased from an average SER of −1 to −9 diopters (FIG. 3A). A one-way analysis of variance was used to test for an association between haplotype and spherical equivalent refraction (SER); there was a highly significant association ($p<0.0001$).

The L:M cone ratio of eleven of the subjects from FIG. 3A was estimated using flicker photometric ERG and individualized cone spectra (J. Carroll, C. McMahon, M. Neitz, J. Neitz, *Journal of the Optical Society of America A* 17, 499 (March, 2000)). For each of the 11 subjects, the predicted SER was calculated by taking the mean SER for the haplotype group from FIG. 3A, and scaling it according to the percentage of L plus M cones that were L cones for each subject. For example, if a person had haplotype 8 (FIG. 3A), their myopic potential was −4.5 diopters. If that person had a 1:1 cone ratio they would be expected to have the full −4.5 diopters of refractive error. However, if he had nearly 100 percent L cones he would be expected to be nearly emmetropic. 75% L cones falls midway between a 1:1 cone ratio (50% L) and 100% L so a person with haplotype 8 and 75% L cones would be predicted to have 50% of the SER (or −4.5/2=2.25 diopters).

The SER for each subject was compared to the SER predicted by the combined haplotype and cone ratio data (FIG. 3B). The correlation coefficient ($R^2$) was 0.86, suggesting that 86% of the SER could be predicted by knowing the Xq28 opsin gene locus haplotype and the L:M cone ratios for each subject in this sample. L:M cone ratio is also encoded by genetic variation in the X-linked opsin gene array.

Example 3

Red Content of Video Games Causes Increased Refractive Error

Figure 4:
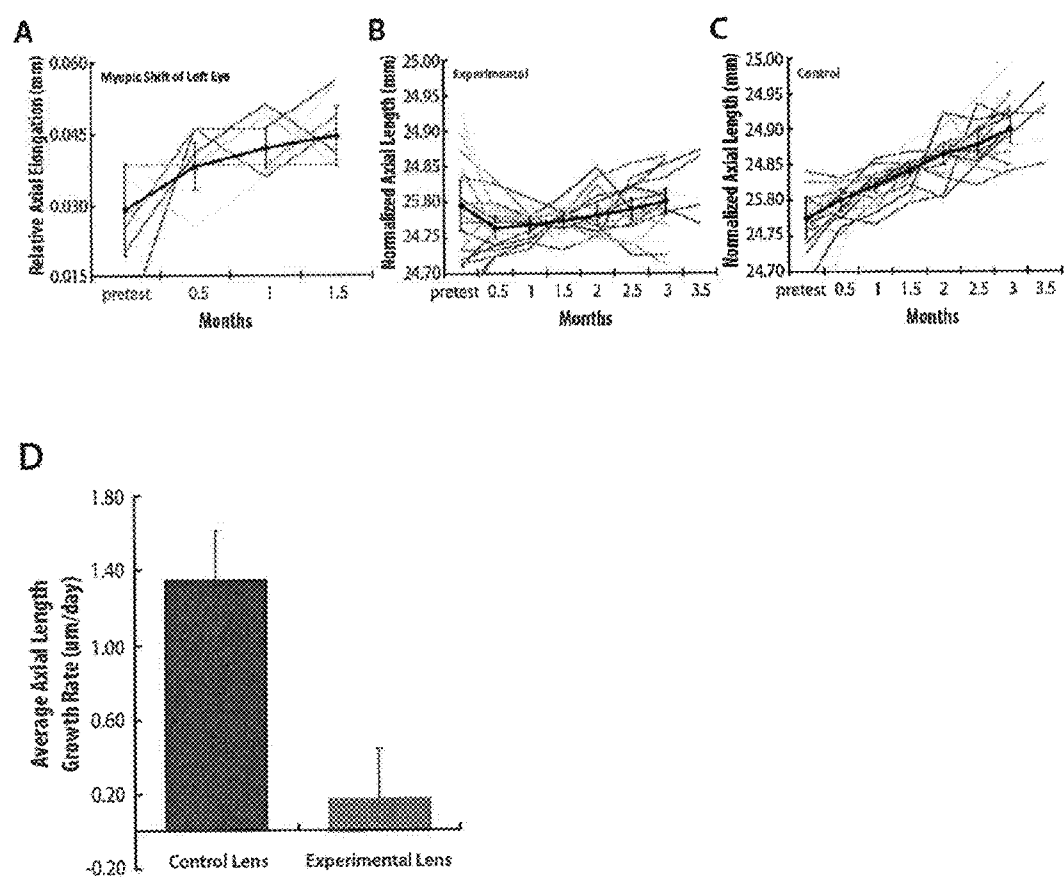
FIG. 4. (A) Myopic shift produced by exposure to the red light for 2 hours per day. Axial lengths were measured for each subject before the onset of the experimental procedure. Subsequently, each subject played a black and white video game for 2 hours per day while wearing goggles with the right lens untinted and the left lens tinted so that the L cones are activated much more than M cones. (B) Normalized axial length measurements as a function of time for 20 eyes wearing the experimental lens and (C) for 20 fellow eyes that served as the controls for each experimental eye. Black lines with error bars represent the averages for all eyes (error bars±2 SEM). The experimental lenses significantly reduced the rate of eye growth of myopic children. (D) Growth rate of eyes wearing the experimental lens are to the left, and for eyes wearing the control lens are to the right.

The potential for the red content of video games to contribute to myopia was evaluated as follows. Baseline axial length measurements were obtained for seven 18 year old subjects, and at 2 week intervals thereafter, for 2 months during which time each subject played a video game for 1 hour per day while wearing special goggles. The video game was in black and white, and while playing the game, subjects viewed the computer monitor through a pair of goggles in which the right lens was clear so that the L and M cones were nearly equally activated, and the left lens was tinted such that only the L but not the M cones were activated. The data plotted in FIG. 4A shows the trend line of a significant myopic shift (p=0.0076) in the left eye that viewed the red video games relative to the right control eye of the subjects. The increased axial length of eye exposed to the red relative to black and white video game corresponds to an increase in refractive error of ⅓ of a diopter per year.

Example 4

Glasses that Control the Spectral Distribution of Light Reaching the Retina can Prevent Myopia The ability of modified eyeglasses to influence the growth of the axial length of the eye when routinely worn by children was evaluated. Both lenses of the study eyeglasses had the optimal correction for each subject as determined by the participant's optometrist. One lens in each pair of glasses was the experimental lens, which was tinted and had a holographic diffuser applied to the surface. The tint removed red light and the diffuser spread the incident light rays over an angle of 0.5 degree to produce a slight blur to reduce activity differences between adjacent cones. The other lens in each pair of glasses was a control lens that was tinted with a neutral filter that equally activated L and M cones, and was chosen so that both eyes were exposed to the same light intensity. The dominant eye was identified for each subject, and for the first 3 month period, all subjects wore the experimental lens on the dominant eye. Subjects were offered the opportunity to re-enroll after 3 months, and those who chose to re-enroll wore the experimental lens over the non-dominant eye during the second 3 month period.

Before participants began wearing the experimental glasses, the axial lengths of both eyes were measured using the Zeiss IOL Master, which has been established previously to produce accurate and reproducible measurements in children, with a standard deviation between repeated measures of axial length in children of ±0.019 (A. Carkeet, S. M. Saw, G. Gazzard, W. Tang, D. T. Tan, *Optometry and Vision Science* 81, 829 (2004); J. Gwiazda et al., *Investigative Ophthalmology & Visual Science* 44, 1492 (2003)). Each axial length measurement plotted in FIG. 4 was the average of twenty measurements for each eye. General baseline characteristics of the thirteen subjects enrolled in the study are given in Table 2. Spherical equivalent refraction (SER) was determined for both eyes at the beginning of the study, and axial length measurements were determined for each eye the day that the children received their modified eye glasses. The values given were the average of twenty measurements for each eye. The last column indicates which eye had the experimental Versus control lens (OS left eye, OD right eye).

TABLE 2

| Subject ID No. | Gener | Age | SER (OD) | SER (OS) | Axial Length (mm) (OD) | Axial Length (mm) (OS) | Experimental Control |
|---|---|---|---|---|---|---|---|
| 001 | F | 12 | −1.50 | −1.50 | 25.18 | 25.27 | OD/OS |
| 002 | F | 13 | −3.75 | −3.25 | 24.76 | 24.95 | OS/OD |
| 003 | F | 14 | −7.875 | −8.125 | 27.53 | 27.84 | OD/OS |
| 004 | M | 11 | −3.25 | −3.25 | 23.96 | 23.93 | OS/OD |
| 005 | F | 9 | −2.75 | −3.00 | 24.80 | 24.86 | OS/OD<br>OD/OS |
| 006 | F | 11 | −1.50 | −1.375 | 22.93 | 23.08 | OS/OD<br>OD/OS |
| 007 | M | 8 | −1.50 | −1.50 | 25.25 | 25.17 | OD/OS<br>OS/OD |
| 008 | M | 13 | −1.75 | −1.50 | 24.39 | 24.54 | OD/OS<br>OS/OD |
| 009 | F | 10 | −2.125 | −2.125 | 25.88 | 25.98 | OS/OD<br>OD/OS |
| 010 | F | 11 | −1.375 | −1.375 | 24.15 | 24.10 | OS/OD |
| 011 | M | 8 | −1.50 | −1.50 | 24.08 | 24.09 | OD/OS |
| 012 | M | 11 | −1.125 | −1.25 | 23.21 | 23.46 | OS/OD<br>OD/OS |
| 013 | M | 12 | −4.00 | −3.75 | 25.85 | 25.77 | OS/OD<br>OD/OS |

All participants completed the study with the dominant eye as the experimental eye and the other eye as an internal control. Seven participants re-enrolled to complete the study a second time, but with the experimental lens on the non-dominant eye. Which lens, and therefore, which eye, had the experimental versus control lens is listed in Table 2. Initial, spherical equivalent refraction (SER) was measured by cycloplegic autorefraction to determine eligibility for the study, and it ranged from a minimum of −1.00 to a maximum of −8.50 diopters. Baseline axial lengths ranged from 22.93 to 27.53 millimeters (mm) for the right eye (OD) and from 23.08 to 27.84 mm for the left eye (OS).

Axial length growth was the primary outcome measure used to evaluate the effect of the experimental lens versus the control lens over the course of three months. The relative growth of axial length was determined for the twenty eyes wearing the experimental lens and for the twenty eyes wearing the control lens. Growth curves for each of the twenty trials demonstrated the dramatic difference in the experimental versus the control group (FIGS. 4B and C). Growth curves for eyes that wore the experimental lens clustered around baseline representing a reduction in elongation of the eye, whereas growth curves for eyes that wore the control lens deviated toward positive growth, representing continued elongation of the eye. Sixteen of the twenty trials followed this growth pattern, where the experimental lens reduced growth and the control lens had continued growth. Overall, normalized differences in axial length between the control and experimental eyes were evaluated by a paired 2-sample t test. Absolute difference in growth between the two eyes reached statistical significance by day 30, as a group. Individually, the date where the growth difference between the two eyes reached significance ranged from day 30 to day 75.

The rate of axial elongation tier eyes wearing experimental versus control lenses was also evaluated (FIG. 4D). The average axial length growth rate in the eyes wearing the experimental lens was 0.063±0.33 μm/day (mean±SE), whereas the average axial length growth rate in the eyes wearing the control lens was 1.43±0.24 μm/day. Again, sixteen of the twenty trials resulted in reduced rate of axial elongation for the eye wearing the experimental lens versus the eye wearing the control lens. Reduction in the overall growth rate in the experimental group relative to the control group was statistically significant (p=0.01019, FIG. 4D).

On average, the eyes wearing the experimental lens grew nearly ten times slower than eyes wearing the control lens.

METHODS

Color Vision Testing: Participants were screened for the presence of an inherited red-green color vision deficiency using the Nagel anomaloscope and the Richmond HRR 2004 edition pseudoisochromatic plate test.

Determination of L:M cone ratios cone ratios were estimated using flicker photometry and genetics as previously described (H. Hofer, J. Carroll, J. Neitz, M. Neitz, D. R. Williams, *Journal of Neuroscience* 25, 9669 (October, 2005); J. Carroll, C. McMahon, M. Neitz, J. Neitz, *Journal of the Optical Society of America A* 17, 499 (March, 2000)).

Adaptive Optics Imaging: Images of retinas were obtained using adaptive optics as described previously (J. Carroll, M. Neitz, H. Hofer, J. Neitz, D. R. Williams, *Proceedings of the National Academy of Sciences of the United States of America* 101, 8461 (2004); J. Carroll et al., *Proceedings of the National Academy of Sciences of the United States of America* 106, 20948 (2009); J. Carroll et al., *Proc. Natl. Acad. Sci. USA* submitted (2010)).

Axial length, corneal curvature, and spherical equivalent refraction (SER): Axial lengths and corneal curvatures for both eyes will be measured for each subject using the Zeiss IOL Master, and the predicted spherical equivalent refraction (SERs) were calculated using a formula derived from a linear regression of a dataset of actual SERs, axial lengths (AL) and corneal curvatures (CC) from a group of 400 male subjects. The formula is: $SER=-(AL*2.03+0.94*CC)+88.58$, where the value for AL was the average of 20 measurements per eye, and CC was the average of two different methods of measuring corneal curvature. Measurements were made for both eyes.

Genetic analysis: DNA was isolated from whole blood or from buccal swabs use the PureGene kit. The polymerase chain reaction was used to selectively amplify the OPN1LW and the OPN1MW genes, and exons 2, 3, and 4 were directly sequenced as previously described (M. Neitz et al., *Visual Neuroscience* 21, 205 (2000)). Quantitative real time PCR was performed on a DNA sample from each subject to estimate the relative number of OPN1LW and OPN1MW genes using previously described assays (M. Neitz, J. Neitz, *Color Research & Application* 26, S239 (2001)).

Human Subjects Research: All human subjects research was conducted under IRB approved protocols at the Medical College of Wisconsin and followed the tenets of the Declaration of Helsinki.

Knock-in/Knock-out mouse constructs. The targeting vector was designed to replace the endogenous mouse OPN1MW gene on the X-chromosome with a human L opsin cDNA. The 5' homology arm was 11,917 bp in length extends from nucleotide position 71,366,218 which is upstream of the OPN1MW gene on the mouse X-chromosome through codon 65 of exon 2 of the mouse OPN1MW gene (nucleotide position 71,378,135 July 2007 version of mouse genome assembly). Site directed mutagenesis (QuickChange Kit, Stratagene) was used to alter mouse codons 58, 62, and 65 to encode the same amino acids as the corresponding codons in human OPN1LW. Amino acids 58 and 62 do not vary among human OPN1LWs but codons 65 does, and in our construct this codon specifies threonine (T65). Mouse codon 58 was changed from ACC to GTC, mouse codon 62 was changed from CIT to TTT, and mouse codon 65 was changed from GTT to ACT. A human cDNA segment from plasmid hs7 (M. Drummond-Borg, S. S. Deeb, A. G. Motulsky, *Proceedings of the National Academy or Sciences of the United States of America* 86, 981 (1989)) extending from codon 66 through the polyadenylation signal (nucleotide 1679 in plasmid hs7 plus 142 base pairs of the polylinker from hs7 was ligated in frame to the 5' homology arm. A PGK-NEO cassette flanked by lox P sites was ligated downstream of the human cDNA fragment, and downstream of that was ligated the 3' homology arm extending from mouse X-chromosome nucleotide 71,389,460 to 71,392,250. The 3' homology arm corresponds to a 2823 base pair segment within intron 5 of the mouse OPN1MW gene. All vectors were confirmed by direct sequencing of the complete vector. Creation of the final vector used and of the knock-in/knock-out mice was done by Ozgene Inc. The targeting constructs were electroporated into embryonic stem cells, and Neomycin resistant cells were screened by Southern Hybridization for correctly targeted events and confirmed by sequencing. Mice showing germline transmission of the correctly targeted locus were mated to Cre mice to delete the PGK Neo cassette. Animals were screened by PCR for the final altered locus, and confirmed by direct sequencing. Upon receiving founder mice from Ozgene, genomic DNA from each mouse was sequenced to confirm the presence of the correctly targeted locus.

Gene expression at the targeted locus was controlled by the endogenous mouse regulatory DNA sequences, and the N terminal tail of the encoded opsin corresponded to that encoded by mouse exon 1. The portion of the N terminus encoded by exon 1 differed from human in that amino acids 4 thru 8 were deleted and the sequence differed at 7 other positions as follows: threonine instead of alanine at position 11, glutamic acid instead of arginine at position 13, glutamine instead of histidine at position 14, threonine in place of proline at position 15, leucine instead of glutamine at position 16, histidine instead of serine at position 18, and lysine instead of arginine at position 37. Human L opsins vary at amino acid positions 65, 111 and 116 encoded by exon 2 and 230, 233 and 236 encoded by exon 4. The targeted locus specified T65, I116, S116, I230, A233 and M236. Two versions of the targeted locus were constructed regarding the amino acid sequence specified by exon 3. The control locus specified L153, I171, A174, I178, S180 (LIAIS) which corresponds to the sequence found in chimpanzee L opsins, and mutant under study specified L153, V171, A174, V178, A180 (LVAVA).

Mouse ERGs: Mice were anesthetized with ketamine/xylazine and kept on a warming table throughout the experiment. The recording electrode was placed on the cornea, the reference electrode was placed under the lid and the ground electrode was touching the tongue. ON-OFF ERGs (alternating 30s ON 30s OFF) were performed using 525 nm LED stimuli at 5 different light intensities (0.3 log intensity steps) controlled by pulse width modulation. The 525 nm lights produce responses mediated by human L cone opsin encoded by the transgenes but not endogenous mouse UV opsin. Recording was performed under light adapted conditions in which rods were saturated.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of determining the opsin haplotype of a subject, said method comprising:

(a) detecting opsin haplotype 1 as set forth in Table 1 in a biological sample obtained from the subject, wherein said haplotype 1 comprises an L-opsin gene encoding an L-opsin polypeptide having a methionine (M) at residue 153, an isoleucine (I) at residue 171, an I at residue 178, a serine (S) at residue 180, and an M at residue 236, and an M-opsin gene encoding an M-opsin polypeptide having an M at residue 153, a valine (V) at residue 171, a V at residue 178, and an alanine (A) at residue 180; and wherein said detecting comprises (i) amplifying and sequencing exons 2, 3, and 4 of the L-opsin opsin gene, and (ii) amplifying and sequencing exons 2, 3, and 4 of the M-opsin opsin gene.

2. The method of claim 1, wherein said biological sample is selected from the group consisting of blood, saliva, cells from buccal swabbing, biopsies of skin, and amniotic fluid.

3. The method of claim 1, further comprising purifying nucleic acids from said biological sample.

4. The method of claim 3, wherein said nucleic acids comprise genomic DNA.

5. The method of claim 1, wherein said amplifying steps comprise polymerase chain reaction (PCR).

6. The method of claim 1, further comprising:

determining the ratio of L-cones to M-cones in the subject, wherein said determining comprises an electroretinogram.

7. The method of claim 6, wherein said electroretinogram is a flicker photometric electroretinogram.

8. A method comprising:

(a) detecting haplotype 1 as set forth in Table 1 in a biological sample obtained from a subject, wherein said haplotype 1 comprises an L-opsin gene encoding an L-opsin polypeptide having a M at residue 153, an I at residue 171, an I at residue 178, a S at residue 180, and an M at residue 236, and an M-opsin gene encoding an M-opsin polypeptide having an M at residue 153, a Vat residue 171, a Vat residue 178, and an A at residue 180;

(b) determining the subject is susceptible to increased myopic potential when haplotype 1 is detected; and (c) treating the subject determined to have increased myopic potential with at least one lens that reduces myopia progression.

9. The method of claim 8, wherein said lens is a glasses lens or a contact lens.

10. The method of claim 8, wherein said lens is a blur-inducing lens.

11. The method of claim 8, wherein said lens comprises a holographic diffuser.

12. The method of claim 11, wherein said holographic diffuser is applied to a surface of said lens.

13. The method of claim 8, wherein said lens is tinted.

14. The method of claim 1, said method further comprising detecting one of haplotypes 2 to 13 as set forth in Table 1 in the biological sample obtained from the subject, wherein said haplotype 2 comprises an L-opsin gene encoding an L-opsin polypeptide having a M at position 153, a V at position 171, an I at position 178, a S at position 180, and a M at position 236, and an M-opsin gene encoding an M-opsin polypeptide having a M at position 153, a V at position 171 and at position 178, and an A at position 180;

wherein said haplotype 3 comprises an L-opsin gene encoding an L-opsin polypeptide having a leucine (L) at position 153, V at position 171, an I at position 178, a S at position 180, and a M at position 236, and an M-opsin gene encoding an M-opsin polypeptide having a M at position 153, a V at position 171 and at position 178, and an A at position 180;

wherein said haplotype 4 comprises an L-opsin gene encoding an L-opsin polypeptide having a M at position 153, a V at position 171, an I at position 178, a S at position 180, and a M at position 236, and an M-opsin gene encoding an M-opsin polypeptide having a M at position 153, a V at position 171, an I at position 178, and an A at position 180;

wherein said haplotype 5 comprises an L-opsin gene encoding an L-opsin polypeptide having a L at position 153, a V at position 171, an I at position 178, an A at position 180, and a M at position 236, and an M-opsin gene encoding an M-opsin polypeptide having a M at position 153, a V at position 171, an I at position 178, and an A at position 180;

wherein said haplotype 6 comprises an L-opsin gene encoding an L-opsin polypeptide having a M at position 153, a V at position 171, an I at position 178, an A at position 180, and a M at position 236, and an M-opsin gene encoding an M-opsin polypeptide having a M at position 153, a V at position 171, an I at position 178, and an A at position 180;

wherein said haplotype 7 comprises an L-opsin gene encoding an L-opsin polypeptide having a L at position 153, a V at position 171, an I at position 178, a S at position 180, and a M at position 236, and an M-opsin gene encoding an M-opsin polypeptide having a L or a M at position 153, a V at position 171, an I at position 178, and an A at position 180;

wherein said haplotype 8 comprises an L-opsin gene encoding an L-opsin polypeptide having a L at position 153, a V at position 171, an I at position 178, a S at position 180, and a M at position 236, and an M-opsin gene encoding an M-opsin polypeptide having a M at position 153, a V at position 171, an I at position 178, and an A at position 180;

wherein said haplotype 9 comprises an L-opsin gene encoding an L-opsin polypeptide having a L at position 153, an I at position 171, an I at position 178, a S at position 180, and a M at position 236, and an M-opsin gene encoding an M-opsin polypeptide having a M at position 153, a V at position 171, a V at position 178, and an A at position 180;

wherein said haplotype 10 comprises an L-opsin gene encoding an L-opsin polypeptide having a M at position 153, a V at position 171, a V at position 178, an A at position 180, and a V at position 236, and an M-opsin gene encoding an M-opsin polypeptide having a M at position 153, a V at position 171, an I at position 178, and an A at position 180;

wherein said haplotype 11 comprises an L-opsin gene encoding an L-opsin polypeptide having a M at position 153, a V at position 171, an I at position 178, a S at position 180, and a V at position 236, and an M-opsin gene encoding an M-opsin polypeptide having a M at position 153, a V at position 171, a V at position 178, and an A at position 180;

wherein said haplotype 12 comprises an L-opsin gene encoding an L-opsin polypeptide having a L at position 153, a V at position 171, an I at position 178, a S at position 180, and a M at position 236, and an M-opsin gene encoding an M-opsin polypeptide having a L at position 153, a V at position 171, an I at position 178, and a S at position 180;

wherein said haplotype 13 comprises an L-opsin gene encoding an L-opsin polypeptide having a L at position 153, a V at position 171, an I at position 178, an A at position 180, and a M at position 236, and an M-opsin gene encoding an M-opsin polypeptide having a L or a M at position 153, a V at position 171, an I at position 178, and an A at position 180; and wherein said detecting comprises (i) amplifying and sequencing exons 2, 3, and 4 of the OPN1LW gene in an opsin array, and (ii) amplifying and sequencing exons 2, 3, and 4 of the OPN1MW gene in an opsin array.

15. The method of claim 8, said method further comprising:

detecting one of haplotypes 2 to 13 as set forth in Table 1 in the biological sample obtained from the subject;

wherein said haplotype 2 comprises an L-opsin gene encoding an L-opsin polypeptide having a M at position 153, a V at position 171, an I at position 178, a S at position 180, and a M at position 236, and an M-opsin gene encoding an M-opsin polypeptide having a M at position 153, a V at position 171 and at position 178, and an A at position 180;

wherein said haplotype 3 comprises an L-opsin gene encoding an L-opsin polypeptide having a leucine (L) at position 153, V at position 171, an I at position 178, a S at position 180, and a M at position 236, and an M-opsin gene encoding an M-opsin polypeptide having a M at position 153, a V at position 171 and at position 178, and an A at position 180;

wherein said haplotype 4 comprises an L-opsin gene encoding an L-opsin polypeptide having a M at position 153, a V at position 171, an I at position 178, a S at position 180, and a M at position 236, and an M-opsin gene encoding an M-opsin polypeptide having a M at position 153, a V at position 171, an I at position 178, and an A at position 180;

wherein said haplotype 5 comprises an L-opsin gene encoding an L-opsin polypeptide having a L at position 153, a V at position 171, an I at position 178, an A at position 180, and a M at position 236, and an M-opsin gene encoding an M-opsin polypeptide having a M at position 153, a V at position 171, an I at position 178, and an A at position 180;

wherein said haplotype 6 comprises an L-opsin gene encoding an L-opsin polypeptide having a M at position 153, a V at position 171, an I at position 178, an A at position 180, and a M at position 236, and an M-opsin gene encoding an M-opsin polypeptide having a M at position 153, a V at position 171, an I at position 178, and an A at position 180;

wherein said haplotype 7 comprises an L-opsin gene encoding an L-opsin polypeptide having a L at position 153, a V at position 171, an I at position 178, a S at position 180, and a M at position 236, and an M-opsin gene encoding an M-opsin polypeptide having a L or a M at position 153, a V at position 171, an I at position 178, and an A at position 180;

wherein said haplotype 8 comprises an L-opsin gene encoding an L-opsin polypeptide having a L at position 153, a V at position 171, an I at position 178, a S at position 180, and a M at position 236, and an M-opsin gene encoding an M-opsin polypeptide having a M at position 153, a V at position 171, an I at position 178, and an A at position 180;

wherein said haplotype 9 comprises an L-opsin gene encoding an L-opsin polypeptide having a L at position 153, an I at position 171, an I at position 178, a S at position 180, and a M at position 236, and an M-opsin gene encoding an M-opsin polypeptide having a M at position 153, a V at position 171, a V at position 178, and an A at position 180;

wherein said haplotype 10 comprises an L-opsin gene encoding an L-opsin polypeptide having a M at position 153, a V at position 171, a V at position 178, an A at position 180, and a V at position 236, and an M-opsin gene encoding an M-opsin polypeptide having a M at position 153, a V at position 171, an I at position 178, and an A at position 180;

wherein said haplotype 11 comprises an L-opsin gene encoding an L-opsin polypeptide having a M at position 153, a V at position 171, an I at position 178, a S at position 180, and a V at position 236, and an M-opsin gene encoding an M-opsin polypeptide having a M at position 153, a V at position 171, a V at position 178, and an A at position 180;

wherein said haplotype 12 comprises an L-opsin gene encoding an L-opsin polypeptide having a L at position 153, a V at position 171, an I at position 178, a S at position 180, and a M at position 236, and an M-opsin gene encoding an M-opsin polypeptide having a L at position 153, a V at position 171, an I at position 178, and a S at position 180;

wherein said haplotype 13 comprises an L-opsin gene encoding an L-opsin polypeptide having a L at position 153, a V at position 171, an I at position 178, an A at position 180, and a M at position 236, and an M-opsin gene encoding an M-opsin polypeptide having a L or a M at position 153, a V at position 171, an I at position 178, and an A at position 180; and determining the subject is susceptible to increased myopic potential when one of haplotypes 2 to 13 as set forth in Table 1 is detected.

* * * * *